US010933218B2

(12) United States Patent
Masi et al.

(10) Patent No.: US 10,933,218 B2
(45) Date of Patent: Mar. 2, 2021

(54) SYSTEMS AND METHODS FOR DELIVERING CHEMICAL AND ELECTRICAL STIMULATION ACROSS ONE OR MORE NEURAL CIRCUITS

(71) Applicant: Massachusetts Institute of Technology, Cambridge, MA (US)

(72) Inventors: Byron C. Masi, New Salem, MA (US); Patrick L. Tierney, Somerville, MA (US); Ann M. Graybiel, Lincoln, MA (US); Michael J. Cima, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1085 days.

(21) Appl. No.: 14/908,586

(22) PCT Filed: Jul. 30, 2014

(86) PCT No.: PCT/US2014/048899
§ 371 (c)(1),
(2) Date: Jan. 29, 2016

(87) PCT Pub. No.: WO2015/017543
PCT Pub. Date: Feb. 5, 2015

(65) Prior Publication Data
US 2016/0166803 A1 Jun. 16, 2016

Related U.S. Application Data

(60) Provisional application No. 61/859,839, filed on Jul. 30, 2013.

(51) Int. Cl.
*A61M 25/00* (2006.01)
*A61B 5/04* (2006.01)
(Continued)

(52) U.S. Cl.
CPC ..... *A61M 25/0043* (2013.01); *A61B 5/04001* (2013.01); *A61B 5/6877* (2013.01);
(Continued)

(58) Field of Classification Search
CPC ...... A61N 1/05; A61N 1/0551; A61N 1/0529; A61N 1/0534; A61N 1/36071;
(Continued)

(56) References Cited

U.S. PATENT DOCUMENTS 4,606,118 A   8/1986  Cannon et al.
5,004,457 A   4/1991  Wyatt et al.
(Continued)

OTHER PUBLICATIONS

International Search Report and Written Opinion of the International Searching Authority for PCT/US2014/048899 dated Feb. 2, 2015.
(Continued)

*Primary Examiner* — Joseph A Stoklosa
*Assistant Examiner* — Brian M Antiskay
(74) *Attorney, Agent, or Firm* — Eversheds Sutherland (US) LLP

(57) ABSTRACT

Systems, devices, and methods are provided for delivering chemical and electrical stimulation across one or more neural circuits. The systems, devices, and methods can also be used for sensing and recording specific neural activity. In certain embodiments, a system includes first and second fluid reservoirs, a manifold, and a delivery tube. The manifold may include first and second chambers therein. The first chamber may be in fluid communication with the first reservoir, and the second chamber may be in fluid communication with the second reservoir. The delivery tube may include a first conduit in fluid communication with the first chamber, a second conduit in fluid communication with the second chamber, and a third conduit configured to house an
(Continued)

electrode therein. In this manner, a distal tip of the delivery tube is configured to be positionable adjacent to the one or more neural circuits for providing chemical and electrical stimulation thereto.

27 Claims, 10 Drawing Sheets

(51) Int. Cl.
| | |
|---|---|
| *A61M 1/12* | (2006.01) |
| *A61N 1/05* | (2006.01) |
| *A61N 1/04* | (2006.01) |
| *A61B 5/00* | (2006.01) |
| *A61N 1/00* | (2006.01) |

(52) U.S. Cl.
CPC ......... *A61N 1/0488* (2013.01); *A61N 1/0529* (2013.01); *A61N 1/0531* (2013.01); *A61N 1/0534* (2013.01); *A61N 1/0551* (2013.01); *A61M 2205/054* (2013.01)

(58) Field of Classification Search
CPC .............. A61N 1/36025; A61N 1/3605; A61N 1/36064; A61N 1/04; A61B 5/04001; A61B 5/4094; A61B 5/0478; A61B 5/0476; A61B 5/04; A61B 5/0031; A61M 1/12; A61M 1/127; A61M 3/0233; A61M 5/1407; A61M 5/1408; A61M 5/1413; A61M 5/16831; A61M 5/19; A61M 5/204; A61M 2005/3132; A61M 39/02; A61M 39/10; A61M 25/00; A61M 2025/0004; A61M 25/0026; A61M 25/0043; A61M 25/007; A61M 2039/0264; A61M 2039/0267; A61M 2039/0036; A61M 2039/0282; A61M 2039/082
USPC ................ 600/372–373, 377–378, 544–545; 607/115–118; 604/80, 85, 93.01, 191, 604/201, 288.01, 306
See application file for complete search history.

(56) References Cited

U.S. PATENT DOCUMENTS

| | | | | |
|---|---|---|---|---|
| 5,081,990 | A | 1/1992 | Deletis | |
| 5,163,902 | A * | 11/1992 | Lynn | A61M 39/04 604/533 |
| 5,190,525 | A * | 3/1993 | Oswald | A61M 5/1408 604/83 |
| 5,192,269 | A * | 3/1993 | Poli | A61M 5/1408 137/606 |
| 5,423,877 | A | 6/1995 | Mackey | |
| 5,458,629 | A | 10/1995 | Baudino et al. | |
| 5,713,923 | A | 2/1998 | Ward et al. | |
| 5,978,702 | A | 11/1999 | Ward et al. | |
| 6,083,205 | A * | 7/2000 | Bourne | A61M 5/1408 137/883 |
| 6,128,537 | A | 10/2000 | Rise | |
| 6,129,685 | A * | 10/2000 | Howard, III | A61N 1/36036 600/373 |
| 6,530,907 | B1 * | 3/2003 | Sugahara | A61M 39/223 604/246 |
| 6,626,902 | B1 | 9/2003 | Kucharczyk et al. | |
| 6,799,074 | B1 * | 9/2004 | Thomas | A61B 90/11 606/130 |
| 7,442,183 | B2 | 10/2008 | Baudino et al. | |
| 7,505,807 | B1 | 3/2009 | Kucharczyk et al. | |
| 7,653,433 | B2 | 1/2010 | Lozano et al. | |
| 8,682,412 | B2 * | 3/2014 | Oh | A61B 5/04001 600/377 |
| 8,788,064 | B2 * | 7/2014 | Mercanzini | A61N 1/0531 600/378 |
| 9,155,861 | B2 | 10/2015 | Hetke et al. | |
| 2004/0204735 | A1 * | 10/2004 | Shiroff | A61B 17/320016 606/190 |
| 2004/0220545 | A1 * | 11/2004 | Heruth | A61M 5/14276 604/508 |
| 2005/0277912 | A1 * | 12/2005 | John | G16H 20/17 604/890.1 |
| 2006/0264897 | A1 | 11/2006 | Lobl et al. | |
| 2007/0106143 | A1 | 5/2007 | Flaherty | |
| 2007/0118197 | A1 | 5/2007 | Loeb | |
| 2008/0195160 | A1 * | 8/2008 | Wingeier | A61N 1/0529 607/3 |
| 2010/0098767 | A1 | 4/2010 | Olbricht et al. | |
| 2010/0201200 | A1 | 8/2010 | Hori | |
| 2010/0241100 | A1 * | 9/2010 | Blumenfeld | A61B 5/0075 604/503 |
| 2010/0324643 | A1 * | 12/2010 | Brabec | A61N 1/0556 607/121 |
| 2011/0184266 | A1 * | 7/2011 | Levin | A61B 5/14503 600/365 |
| 2011/0257715 | A1 | 10/2011 | Jaroch et al. | |
| 2012/0035605 | A1 * | 2/2012 | Tegg | A61B 18/1492 606/41 |
| 2012/0046531 | A1 * | 2/2012 | Hua | A61B 5/6865 600/317 |
| 2012/0053506 | A1 * | 3/2012 | Ludvig | A61B 5/0478 604/9 |
| 2013/0123600 | A1 * | 5/2013 | Tcheng | A61B 5/0478 600/378 |
| 2013/0190851 | A1 * | 7/2013 | Schouenborg | A61N 1/0536 607/116 |
| 2013/0345628 | A1 * | 12/2013 | Berger | A61M 25/007 604/101.05 |

OTHER PUBLICATIONS

Written Opinion of the International Preliminary Examining Authority for PC/US2014/048899 dated Aug. 7, 2015.
Harris, J.P. et al., Mechanically Adaptive Intracortical Implants Improve the Proximity of Neuronal Cell Bodies, J Neural Eng., Dec. 2011, pp. 948-1009, vol. 8(6).
Moshayedi, P. et al., The Relationship Between Glial Cell Mechanosensitivity and Foreign Body Reactions in the Central Nervous System, Biomaterials, 2014, pp. 3919-3925, vol. 35.
Nguyen, J.K. et al., Mechanically-Compliant Intracortical Implants Reduce the Neuroinflammatory Response, J Neural Eng., Oct. 2014, pp. 1-27, vol. 11(5).
Canales, A. et al., Multifunctional Fibers for Simultaneous Optical, Electrical and Chemical Interrogation of Neural Circuits in Vivo, Mar. 2015, pp. 277-286, vol. 33, No. 3.
Lacour, S. et al., Materials and Technologies for Soft Implantable Neuroprostheses, Nature Reviews, Sep. 27, 2016, pp. 1-14.
Dagdeviren, C. et al., Miniaturized Neural System for Chronic, Local Intracerebral Drug Delivery, Sci. Transl. Med., Jan. 24, 2018, pp. 1-10, vol. 10.
Ramadi, K.B. et al., Focal, Remote-Controlled, Chronic Chemical Modulation of Brain Microstructures, PNAS, Jul. 10, 2018, pp. 7254-7259, vol. 115, No. 28.

* cited by examiner

SYSTEMS AND METHODS FOR DELIVERING CHEMICAL AND ELECTRICAL STIMULATION ACROSS ONE OR MORE NEURAL CIRCUITS

CROSS-REFERENCE TO RELATED APPLICATION

The disclosure claims priority to and the benefit of U.S. Provisional Application No. 61/859,839, filed Jul. 30, 2013, which is incorporated by reference herein in its entirety.

FIELD

The disclosure generally relates to medical devices and more particularly relates to systems and methods for delivering chemical and electrical stimulation across one or more neural circuits.

BACKGROUND

There is increasing evidence that the pathology underlying many neurologic disorders is a failure in the dynamic communication between multiple brain areas as opposed to a deficit in a single brain area. This has led to the notion of circuit-based disorders. The conceptual change is more than just semantics. Instead of focusing treatment on the suspected pathological neural tissue, the new therapeutic target is normalizing activity across a circuit. Normalization can be achieved by intervention at any level within the circuit and not just in the brain area where the original insult occurred. The treatment of circuit-based disorders, therefore, is significantly improved by tools that allow for modulating the precise tuning of circuit activity (i.e., reducing activity of an overactive node in the circuit or conversely increasing activity in a node that is pathologically silent). The brain uses both chemical and electrical methods of communication. Combining chemically-based and electrically-based therapeutic approaches, therefore, has great potential advantages for facilitating the fine-tuning of activity across such circuits.

Current micro-cannula devices can be divided into two subsets. The first subset includes devices that have a single lumen. These devices are appealing due to their high aspect ratio (length:diameter, typically 10 cm:250 µm) and structural integrity, which is generally achieved by using stainless steel hypodermic tubing. However, these devices have limited functionality since they only administer one fluid at a time and do not contain onboard electrodes or tetrodes. Switching solutions with single lumen devices undesirably requires expelling the entire dead-volume of the device, which can lead to overdosing or to drug delivery beyond the specifically targeted region of the brain. The second subset of devices includes those that have more diverse functionality engineered into them, such as multiple lumens and on-board electrodes. The merit of these devices is the range of functions (multiple solution infusion and electrophysiology) that are possible with a single device. The brittle materials and methods of manufacture of these devices, however, limit the aspect ratios that can be achieved (5 mm:200 µm). The current state-of-the-art devices of this type are limited to use in rodent models and are not directly scalable to larger animal models or to clinical applications. Accordingly, in order to precisely tune activity across neural circuits, a single device that is capable of delivering drugs while simultaneous performing electrical stimulation is needed.

SUMMARY

Some or all of the foregoing needs and/or problems may be addressed with one or more of the injectrode embodiments of the present disclosure. In certain embodiments, the systems and methods for delivering chemical and electrical stimulation across one or more neural circuits includes first and second fluid reservoirs, a manifold, and a delivery tube. The manifold may include first and second chambers therein. The first chamber may be in fluid communication with the first reservoir, and the second chamber may be in fluid communication with the second reservoir. The delivery tube may include a first conduit in fluid communication with the first chamber, a second conduit in fluid communication with the second chamber, and a third conduit configured to house an electrode therein. In this manner, a distal tip of the delivery tube is configured to be positioned adjacent to the one or more neural circuits for providing chemical and electrical stimulation thereto.

Other features and aspects of the disclosure will be apparent or will become apparent to one with skill in the art upon examination of the following figures and the detailed description. All other features and aspects, as well as other system, method, and assembly embodiments, are intended to be included within the description and are intended to be within the scope of the accompanying claims.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Figure 1:
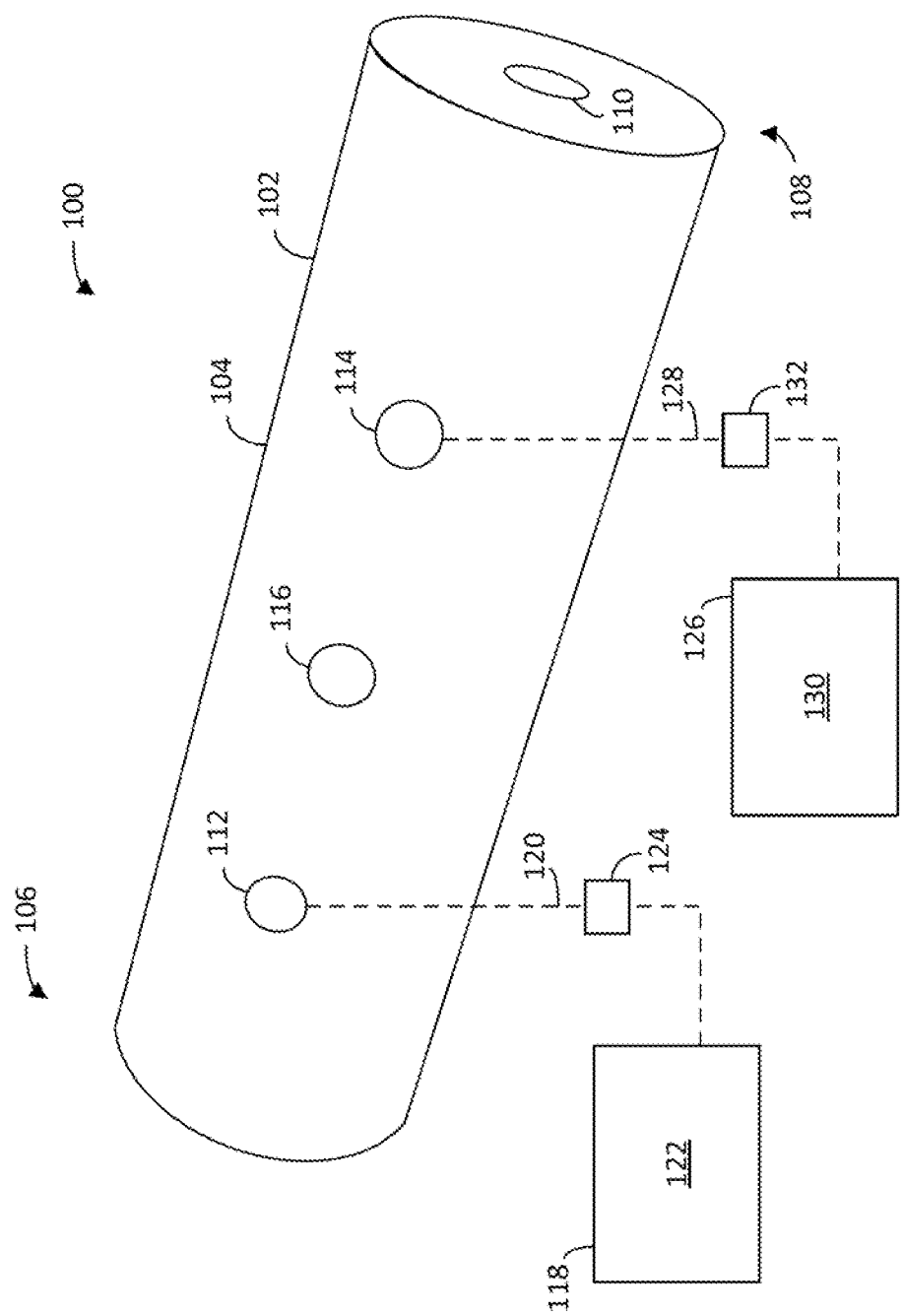
FIG. 1 schematically depicts a perspective view of a manifold in accordance with one or more embodiments of the disclosure.

Systems, devices, and methods have been developed for delivering chemical and electrical stimulation across one or more neural circuits. These systems and devices may also be used for sensing and recording of neural activity. Various embodiments of an injection-microelectrode ("injectrode") are described herein. In some embodiments, the injectrode is a micro-injectrode. In some instances, the injectrode includes a chronic intracranial implant configured to facilitate the administration of both chemical and electrical therapy to specific anatomical (e.g., brain) nuclei.

The system generally is configured to be partially or fully implantable in a patient. The patient may be human or other mammal. In one embodiment, the system includes one or more drug reservoirs and one or more pumps configured for subcutaneously implantation, which may be remote from or adjacent to the injectrode insertion site.

Long-term treatment with oral medications frequently leads to drug tolerance and dose escalation. Due to the large doses usually required, the side effects of these drug treatments often exceed the therapeutic effects, thus eliminating pharmacological treatments as a feasible strategy for many patients. Large numbers of otherwise promising drugs have been set aside for this reason. The injectrode disclosed herein is capable of dosing drug precisely and exclusively to the intended site of action. The amount of drug necessary, therefore, is drastically reduced. This fact, in concert with the synergistic application of electrical stimulation, advantageously can produce reduced incidence of drug tolerance and systemic side effects.

The greater precision in regulating neural circuit activity provided by the injectrode disclosed herein reduces the number and frequency of debilitating side effects common when systemic drugs are administered. It also prolongs the efficacy of deep brain stimulation alone. For example, a drug can be administered to slightly increase the excitability of a brain structure. The result is that lower electrical stimulation currents can be used to modulate activity of that area. Lower currents reduce the occurrence of side effects by limiting the spread of electrical activation to neighboring brain nuclei that may not be part of the targeted circuit. Lower currents may also reduce the potential damage to neural tissue due to heat generation at the injectrode tip. Further, using lower currents prolongs the battery life of stimulators, reducing the number of invasive maintenance procedures.

In certain embodiments, the injectrode disclosed herein is in fluid communication with a first fluid reservoir and a second fluid reservoir. The first and second fluid reservoirs may be configured to supply drugs, chemicals, or other fluids to the injectrode. In this manner, the injectrode may include a manifold in fluid communication with the first and second reservoirs. For example, the manifold may include first and second chambers therein. The first chamber may be in fluid communication with the first reservoir, and the second chamber being in fluid communication with the second reservoir. In one embodiment, the first and/or second reservoir is provided as an implant.

In embodiments, a delivery tube is attached to the manifold. The delivery tube may be configured to deliver drugs and/or electrical stimulation to one or more targeted neural circuits. For example, the delivery tube may include a first conduit in fluid communication with the first chamber and a second conduit in fluid communication with the second chamber. In some instances, the first conduit may include a first access port configured to be positioned within the first chamber, and the second conduit may include a second access port configured to be positioned within the second chamber. Moreover, the delivery tube may include a third conduit configured to house an electrode or other stimulation device. In some instances, the third conduit may include a sensing electrode configured to provide feedback or the like.

In use, a distal tip of the delivery tube is positioned adjacent to the targeted neural circuit in vivo. A first drug may flow from the first reservoir, into the first chamber, down the first conduit, and be delivered to the targeted neural circuit by the distal tip of the delivery tube. Similarly, a second drug may flow from the second reservoir, into the second chamber, down the second conduit, and be delivered to the targeted neural circuit by the distal tip of the delivery tube. In addition, the electrode or other stimulation device positioned within the third conduit may provide electrical stimulation to the targeted neural circuit by way of the distal tip of the delivery tube. The first drug, the second drug, and/or the electrical stimulation may be delivered to the targeted neural circuit separately or simultaneously.

In certain embodiments, the distal tip of the delivery tube is cut and/or polished to produce one or more bevels of a specified angle to minimize tissue damage upon implantation and to improve circuit targeting capabilities. For example, the bevel may be conical or rounded in shape. The distal tip of the delivery tube may be any suitable shape or configuration.

In certain embodiments, the injectrode further includes a guide tube positioned about the delivery tube. The guide tube may provide increased rigidity, durability, and/or targeting capabilities, to the injectrode, particularly to the delivery tube.

In some embodiments, the manifold includes a third chamber positioned between the first chamber and second chamber. The third chamber may be configured to separate the first chamber from the second chamber. For example, the third chamber may comprise an epoxy filled chamber or the like. Moreover, the first chamber, the second chamber, and/or the third chamber may be at least partially separated by one or more silicone septum partitions. In this manner, the delivery tube may be positioned at least partially within the manifold by an introducing needle that may be threaded through the silicone septum partitions. Once the introducing needle is removed, the delivery tube may be at least partially positioned within the manifold, and the silicone septum partitions may form seals between the delivery tube and the first, second, and third chambers.

In one aspect, an injectrode has been developed that achieves several advantages over conventional microcannula electrode devices. In some embodiments, the device disclosed herein combines one or more high aspect ratio fluid conduits, a small drug volume hold up, and/or a small diameter discharge outlet. In this manner, the device advantageously is capable of delivering drugs while simultaneously performing electrical stimulation or detection. The configuration enables delivery of pumped drug in precise amounts with minimal unintended diffusion of drug from the conduit in the static (pump off) state.

In some instances, the injectrode has a manifold that includes at least one chamber therein. The injectrode also may include a delivery tube that comprises at least one conduit configured to be in fluid communication with the at least one chamber. In addition, the injectrode may include at least one electrode conduit configured to house an electrode therein. In some instances, a distal tip of the delivery tube is configured to be positioned adjacent to the one or more neural circuits for providing chemical and electrical stimulation thereto. In an embodiment, each of the one or more conduits has a length of at least about 5 cm and a volume hold up of less than about 10 μL. In another embodiment, the conduit has a length of at least about 10 cm. In yet another embodiment, each of the one or more conduits has a volume hold up from about 1 μL to and about 5 μL. In some instances, the conduit has an outlet at the distal tip end of the delivery tube that has a diameter from about 10 μm to about 100 μm, such as from about 30 μm to about 50 μm. In other instances, the diameter of the outlet is about 40 μm. In one embodiment, the delivery tube is formed of borosilicate glass.

These and other embodiments of the disclosure will be described in more detail through reference to the accompanying drawings in the detailed description of the disclosure that follows. Furthermore, the techniques described above and below may be implemented in a number of ways and in a number of contexts. Several example implementations and contexts are provided with reference to the following figures, as described below in more detail. However, the following implementations and contexts are but a few of many.

FIGS. 1-5 schematically depict an injectrode for delivering chemical and electrical stimulation across one or more neural circuits in accordance with one or more embodiments of the disclosure. Specifically, FIG. 1 depicts a perspective view of a manifold 100 in accordance with one or more embodiments of the disclosure. In certain embodiments, the manifold 100 includes a number of components assembled together. In other embodiments, the manifold 100 is a single unitary structure. The manifold 100 includes a body portion 102 having an elongated cylindrical body 104, which has a first end 106 and a second end 108. The first end 106 and the second end 108 may define a longitudinal length of the elongated cylindrical body 104. The manifold 100 includes a lumen 110 that extends through the elongated cylindrical body 104 from the first end 106 to the second end 108.

The manifold 100 includes a first port 112, a second port 114, and a third port 116 extending from the outer surface of the elongated cylindrical body 104 inward towards the lumen 110. In this manner, the first port 112, the second port 114, and the third port 116 each provide a passageway to the lumen 110. In some instances, the first port 112, the second port 114, and the third port 116 are axially aligned with one another, as shown. In other instances, the first port 112, the second port 114, and the third port 116 may be offset from one another. As will be discussed in greater detail below, the lumen 110 may be partitioned into three separate chambers, with the first port 112 being in fluid communication with the first chamber, the second port 114 being in fluid communication with the second chamber, and the third port 116 being in fluid communication with the third chamber.

In certain embodiments, as shown, the first port 112 is in fluid communication with a first reservoir 118. For example, tubing 120 or the like couples the first reservoir 118 to the first port 112. The first reservoir 118 includes a first drug 122 therein. One or more pumps 124 or the like facilitate the flow of the first drug 122 from the first reservoir 118 to the first port 112. Similarly, the second port 114 is in fluid communication with a second reservoir 126. For example, tubing 128 or the like couples the second reservoir 126 to the second port 114. The second reservoir 126 includes a second drug 130 therein. One or more pumps 132 or the like facilitate the flow of the second drug 130 from the second reservoir 126 to the second port 114.

Figure 2:
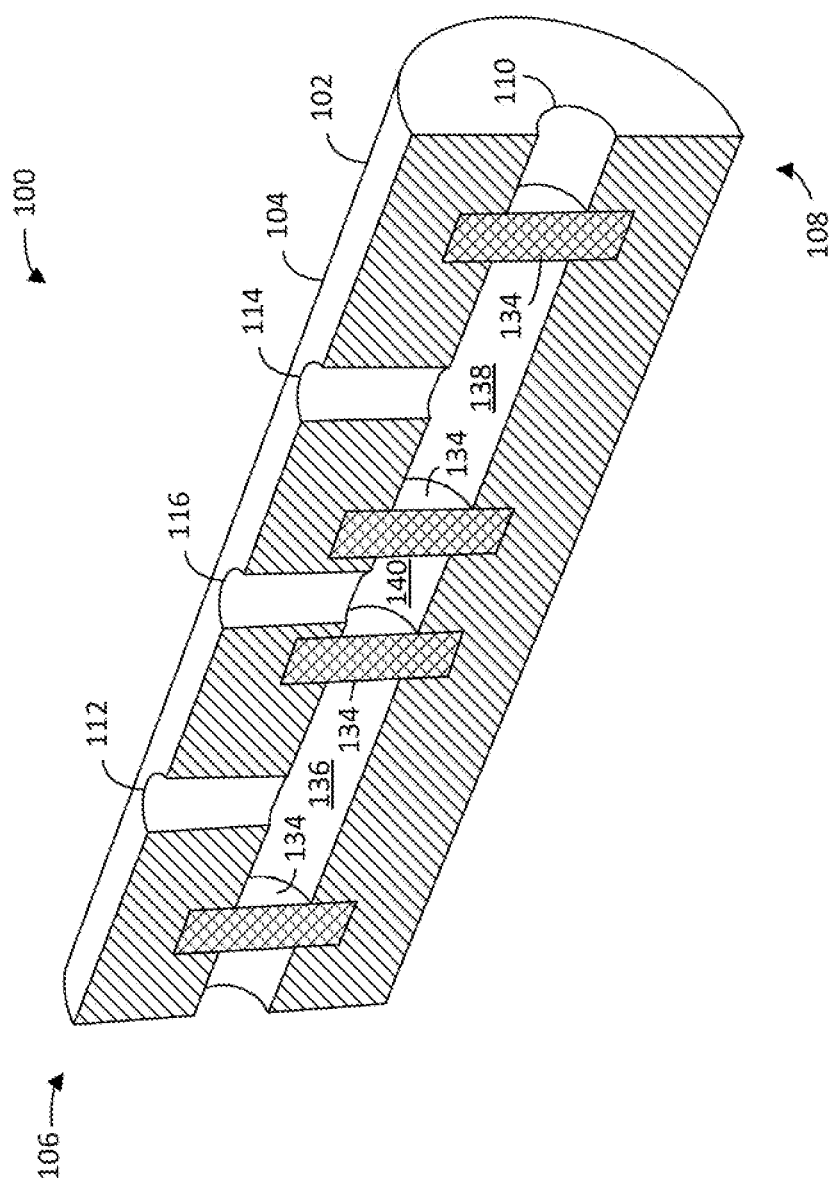
FIG. 2 schematically depicts a cross-sectional perspective view of a manifold in accordance with one or more embodiments of the disclosure.

FIG. 2 schematically depicts a cross-sectional perspective view of the manifold 100 in accordance with one or more embodiments of the disclosure. As depicted in FIG. 2, the lumen 110 extends through the elongated cylindrical body 104 from the first end 106 to the second end 108. A number of silicone septum partitions 134 are positioned within the lumen 110 so as to divide the lumen 110 into a first chamber 136, a second chamber 138, and a third chamber 140. The first chamber 136 is positioned about the first side 106 of the elongated cylindrical body 104, the second chamber 138 is positioned about the second side 108 of the elongated cylindrical body 104, and the third chamber 140 is positioned between the first chamber 136 and the second chamber 138. Moreover, the first port 112 is in fluid communication with the first chamber 136, the second port 114 is in fluid communication with the second chamber 138, and the third port 116 is in fluid communication with the third chamber 140. In this manner, the first chamber 136 may be supplied with the first drug 122 via the first port 112, and the second chamber 138 may be supplied with the second drug 130 via the second port 114. The third chamber 140 may be filled with an epoxy or the like to ensure that the first drug 122 within the first chamber 136 does not mix with the second drug within the second chamber 138. In some instances, the third chamber 140 may be omitted.

Figure 3:
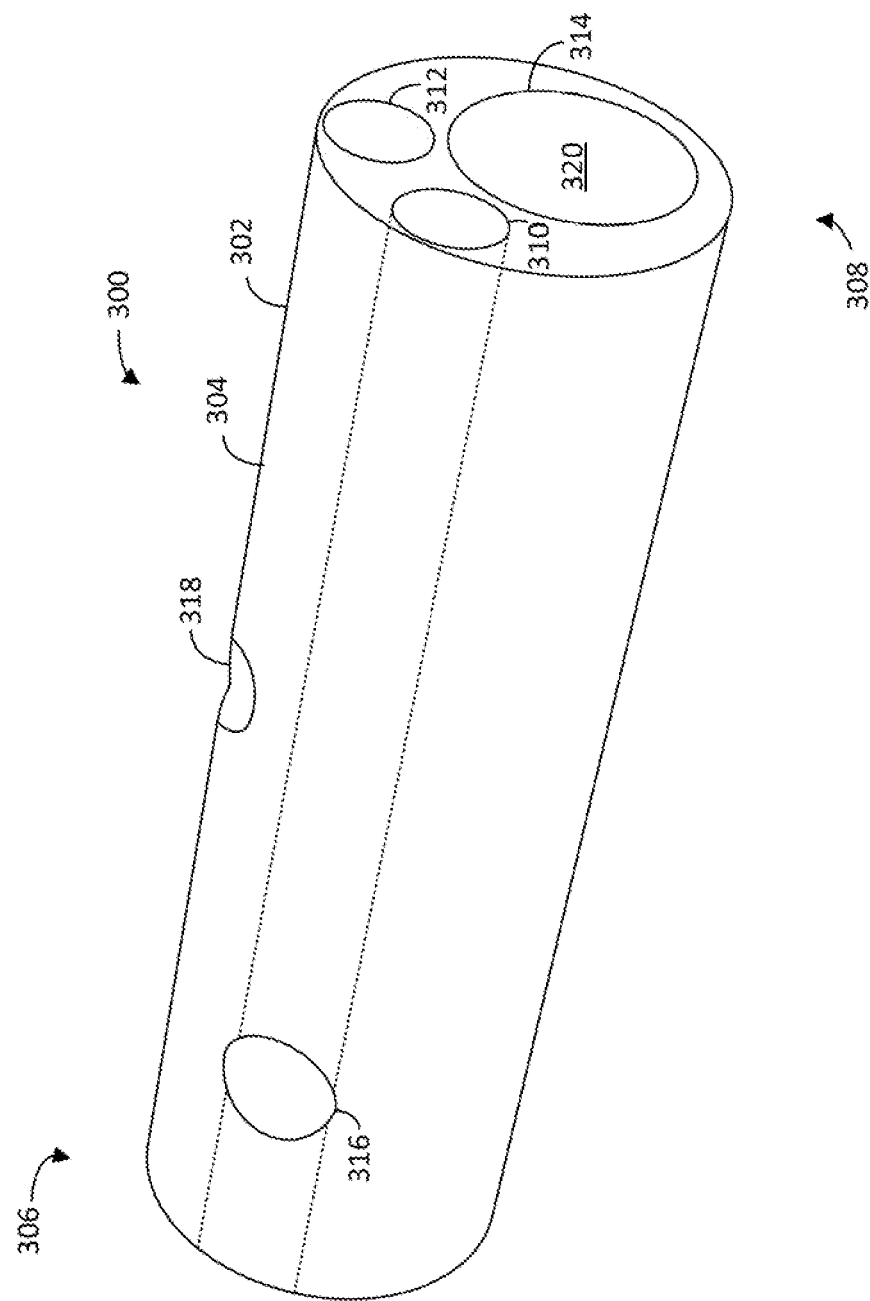
FIG. 3 schematically depicts a perspective view of a delivery tube in accordance with one or more embodiments of the disclosure.

FIG. 3 schematically depicts a perspective view of a delivery tube 300 in accordance with one or more embodiments of the disclosure. The delivery tube 300 may be configured to deliver drugs and/or electrical stimulation to one or more targeted neural circuits. The delivery tube 300 includes a body portion 302. In some instances, as shown, the body portion 302 includes an elongated cylindrical body 304 having a first end 306 and a second end 308. The first end 306 and the second end 308 define a longitudinal length of the elongated cylindrical body 304. In certain embodiments, the delivery tube 300 may be at least partially inserted into the manifold 100. For example, the first end 306 of the delivery tube 300 may be at least partially inserted within the second end 108 or the first end 106 of the manifold 100.

The delivery tube 300 includes a first conduit 310, a second conduit 312, and a third conduit 314, each of which extends through the elongated cylindrical body 304 from the first end 306 to the second end 308. In some instances, as shown, the first conduit 310 includes a first access port 316. The first access port 316 may be positioned within the first chamber 136 of the manifold 100 so as to enable fluid communication between the first chamber 136 and the first conduit 310. In this manner, the first drug 122 may flow from the first reservoir 118, into the first chamber 136, down the first conduit 310, and be delivered to the targeted neural circuit by the second end 308 of the delivery tube 300 (i.e., the distal tip). Similarly, the second conduit 312 includes a second access port 318. The second access port 318 may be positioned within the second chamber 138 of the manifold 100 so as to enable fluid communication between the second chamber 138 and the second conduit 312. In this manner, the second drug 130 may flow from the second reservoir 126, into the second chamber 138, down the second conduit 312, and be delivered to the targeted neural circuit by the second end 308 of the delivery tube 300 (i.e., the distal tip).

As, shown, the third conduit 314 is configured to house (i) an electrode 320 (such as a tungsten wire, a carbon fiber, or the like) or other stimulation device and/or (ii) a sensing device capable of providing neural activity/feedback information, which can be recorded. In some instances, the electrode 320 functions as both a stimulation delivery element and a sensing/recording element. The electrode 320 may provide electrical stimulation to the targeted neural circuit by way of the second end 308 of the delivery tube 300 (i.e., the distal tip). The distal end of the electrode 320 also may be electrically connected to a carbon fiber, e.g., about 7 micrometers in diameter, to facilitate cyclic voltammetry measurements of local neuroactive substance concentrations. Moreover, the electrode 320 may be used to sense and/or record local neural activity to provide feedback to optimize drug delivery parameters based on neural circuit behavior. The first drug 122, the second drug 130, and/or the electrical stimulation may be delivered to the targeted neural circuit separately or simultaneously. In some instances, the first end 306 of the delivery tube 300 may be capped off so as to encourage the flow of fluid to the second end 308 of the delivery tube 300. That is, the first conduit 310 and the second conduit 312 may be plugged or blocked about the first end 306.

In certain embodiments, the delivery tube 300 is composed of borosilicate glass or the like. Moreover, the delivery tube 300 may be about 12 centimeters long and/or about 150 micrometers in diameter. In some instances, the first conduit 310 and the second conduit are about 38 micrometers in diameter and/or the third conduit 314 is about 90 micrometers in diameter. In some embodiments, the electrode 320 includes a tungsten electrode or the like. In an embodiment, the electrode has a diameter of about 75 micrometers. The various components of the injectrode may be any suitable dimension, material, or configuration. Moreover, the various components of the injectrode may be interchanged, omitted, and/or varied in their dimensions.

Figure 4:
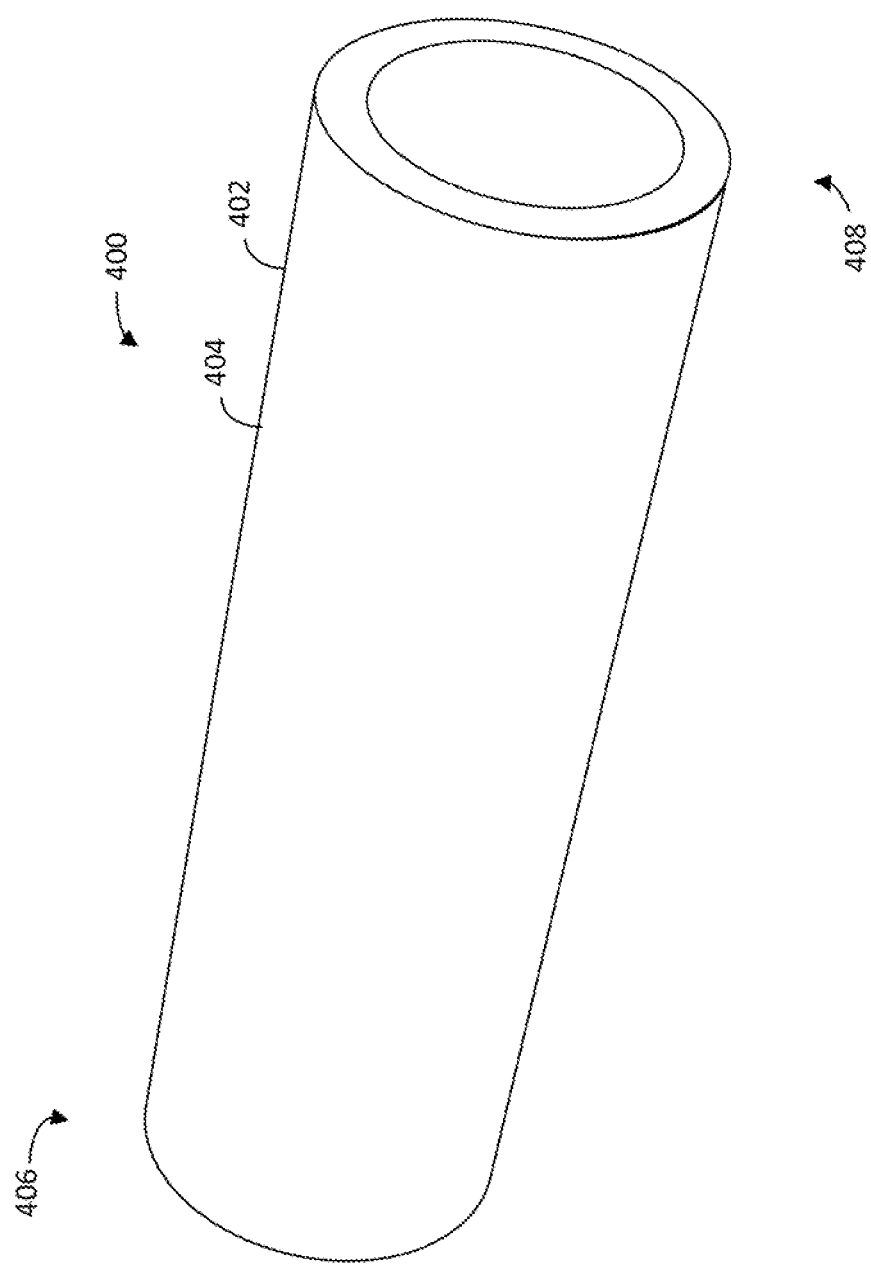
FIG. 4 schematically depicts a perspective view of a guide tube in accordance with one or more embodiments of the disclosure.

FIG. 4 schematically depicts a perspective view of a guide tube 400 in accordance with one or more embodiments of the disclosure. The guide tube 400 may be positioned about the delivery tube 300. That is, the guide tube 400 may wholly or partially encompass the delivery tube 300. The guide tube 400 may provide increased rigidity, durability, and/or targeting capabilities, etc. to the injectrode, particularly to the delivery tube 300. As shown, the guide tube 400 includes a body portion 402. In some instances, as shown, the body portion 402 includes an elongated cylindrical body 404 having a first end 406 and a second end 408. The first end 406 and the second end 408 define a longitudinal length of the elongated cylindrical body 404. In certain embodiments, the guide tube 400 may be at least partially positioned within the manifold 100 and/or about the manifold 100. For example, the first end 406 of the guide tube 400 may be positioned in abutting relation to the second end 108 of the manifold 100. In some instances, the guide tube 400 may comprise a stainless steel tube or the like. Moreover, the guide tube 400 may include an outer diameter of about 200 micrometers. The inner diameter of the guide tube 400 may be such that it fits about the delivery tube 300. The guide tube 400 may be any suitable dimension, material, or configuration.

In certain embodiments, the distal tip of the guide tube 400 is cut and/or polished to produce one or more bevels of a specified angle to minimize tissue damage upon implantation. For example, the bevel may be conical or rounded in shape. The distal tip of the guide tube 400 may be any suitable shape or configuration.

Figure 5:
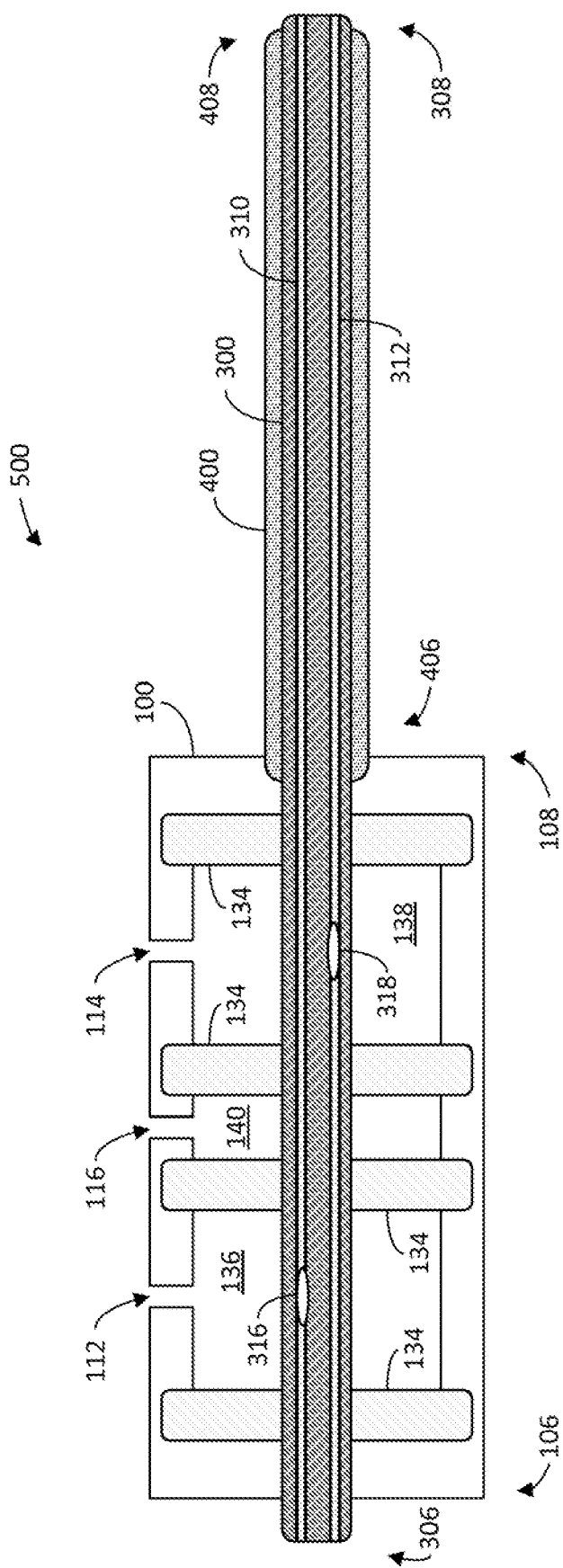
FIG. 5 schematically depicts a cross-sectional top view of an injectrode for delivering chemical and electrical stimulation across one or more neural circuits in accordance with one or more embodiments of the disclosure.

FIG. 5 schematically depicts a cross-sectional top view of an injectrode 500 for delivering chemical and electrical stimulation across one or more neural circuits in accordance with one or more embodiments of the disclosure. As depicted in FIG. 5, the injectrode 500 includes the manifold 100, the delivery tube 300, and the guide tube 400 assembled together. In some instances, however, the guide tube 400 may be omitted and/or additional components may be added.

As shown, the silicone septum partitions 134 are positioned within the manifold 100 so as to define the first chamber 136, the second chamber 138, and the third chamber 140. The first port 112 is in fluid communication with the first chamber 136. The second port 114 is in fluid communication with the second chamber 138. The third port 116 is in fluid communication with the third chamber 140. In this manner, the first chamber 136 may be supplied with the first drug 122 via the first port 112, and the second chamber 138 may be supplied with the second drug 130 via the second port 114. The third chamber 140 may be filled with an epoxy or the like to ensure that the first drug 122 within the first chamber 136 does not mix with the second drug within the second chamber 138. That is, the third chamber 140 may be filled with a material that creates a barrier between the first chamber 136 and the second chamber 138.

The delivery tube 300 may be at least partially positioned within the manifold 100 so as to deliver drugs and/or electrical stimulation to the one or more targeted neural circuits. For example, the first end 306 of the delivery tube 300 is inserted into the second end 108 or the first end 106 of the manifold 100 so that the first access port 316 is positioned within the first chamber 136 and the second access port 318 is positioned within the second chamber 138. In this manner, the first drug 122 may flow from the first reservoir 118, into the first chamber 136, down the first conduit 310, and be delivered to the targeted neural circuit by the second end 308 of the delivery tube 300 (i.e., the distal tip). Similarly, the second drug 130 may flow from the second reservoir 126, into the second chamber 138, down the second conduit 312, and be delivered to the targeted neural circuit by the second end 308 of the delivery tube 300 (i.e., the distal tip). In some instances, the first end 306 of the delivery tube 300 is capped so as to encourage the flow of fluid to the second end 308 of the delivery tube 300. That is, the first conduit 310 and the second conduit 312 may be plugged or blocked about the first end 306.

The third conduit 314 (not shown in FIG. 5) may be configured to house the electrode 320 or another stimulation device. The electrode 320 may provide electrical stimulation to the targeted neural circuit by way of the second end 308 of the delivery tube 300 (i.e., the distal tip). The first drug 122, the second drug 130, and/or the electrical stimulation may be delivered to the targeted neural circuit separately or simultaneously. In some instances, some of the functionality may be omitted. For example, only a single drug may be administered in conjunction with the electrical therapy.

Returning to FIG. 5, the guide tube 400 is positioned about the delivery tube 300. For example, the guide tube 400 may wholly or partially encompass the delivery tube 300. The guide tube 400 may provide increased rigidity, durability, and/or targeting capabilities, etc. to the injectrode 500, particularly to the delivery tube 300. In certain embodiments, the guide tube 400 may be at least partially positioned within the manifold 100 and/or about the manifold 100. For example, the first end 406 of the guide tube 400 may be positioned in abutting relation to the second end 108 of the manifold 100.

Additional reservoirs, ports, chambers, access ports, conduits, and/or electrodes may be incorporated into the injectrode 500. That is, the injectrode 500 may include any number of reservoirs, ports, chambers, access ports, conduits, and/or electrodes. In other embodiment, one or more of the reservoirs, ports, chambers, access ports, conduits, and/or electrodes may be omitted. The illustrated embodiments are but a few of many.

The injectrode 500 may be coated with biocompatible materials or solutions. As discussed above, the injectrode 500 includes three conduits (although more or less conduits may be used) that run axially along the length of the delivery tube 300, allowing for numerous configurations of multiple drug solutions, electrodes, tetrodes, and/or neurochemical sensing probes or the like. The precise combinations of functions can be varied without varying the overall geometry, materials, and/or methods of manufacture of the injectrode 500. This versatility allows for a more efficient and cost effective production of the injectrode 500 as well as a more efficient treatment process. The injectrode 500 can be tailored to the needs of each individual patient using the same or different materials and/or configurations. The injectrode 500 can be manufactured to human length scales while simultaneously and advantageously maintaining a small (>about 1 microliter) fluid hold-up volume.

Conventional neural probes are limited in chronic settings due to the natural formation of a glial scar around the implant. The glial scar manifests as a dense sheath surrounding the implant and is a result of astrocytes and microglia reacting with the foreign material. Scar formation is more robust immediately after the implantation due to tissue trauma and disrupted vasculature immediately surrounding the implant but persists beyond the initial injury due to the constitutive presence of astrocytes and microglia within the brain. Conventional neural probes fail because the sheath eventually excludes neurons from the immediate vicinity of the implant, thus preventing electrical interaction between the implant and neurons. Fibrous encapsulation does not, however, prevent or diminish drug delivery from chronically implanted devices. See, e.g., Farra, R., et al., *First-in-Human Testing of a Wirelessly Controlled Drug Delivery Microchip*. Sci Transl Med, 2012. 4 (122): p. 122ra21. Accordingly, the chemical functionality of the injectrode 500 will persist throughout glial scar formation, whereas all functionality of conventional neural probes would eventually be lost. Biochemical coatings incorporated into the injectrode 500 may be used to diminish the incidence and extent of glial scar formation, thus prolonging even the electrical functionality of the injectrode 500 and generally improving device:host tissue interactions.

By way of example, the injectrode 500 can be a valuable tool in neurological research aimed at understanding the interconnectivity of anatomically distinct nuclei within the healthy or diseased brain. The injectrode 500 can be used to study the pathological origin and dysfunction of neural circuits in anxiety, mood disorders, parkinsonism and related disorders/diseases. The injectrode 500 may be suited to be utilized in a range of mammalian organisms including, but not limited to, rodents, non-human primates, and/or humans. The injectrode 500 can be used to administer precise, variable doses of chemical and electrical therapy to anatomically specific regions of the brain. This capability can be utilized to treat circuit disorders including, but not limited to, anxiety, mood disorders, and Parkinson's disease.

Figure 6:
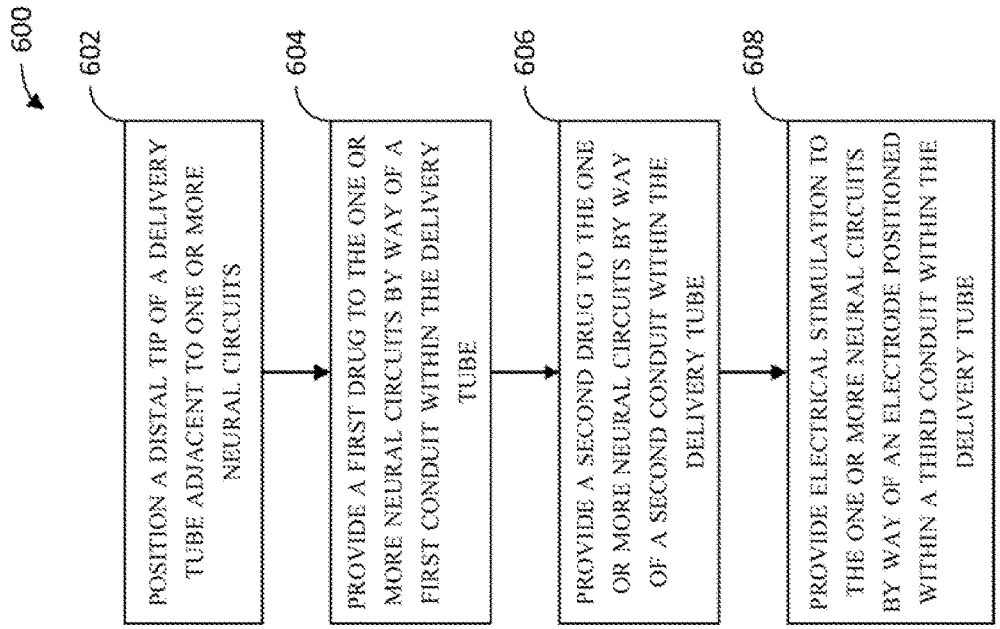
FIG. 6 is a flow diagram depicting an illustrative method for delivering chemical and electrical stimulation across one or more neural circuits in accordance with one or more embodiments of the disclosure.

FIG. 6 is a flow diagram depicting an illustrative method 600 for delivering chemical and electrical stimulation across one or more neural circuits in accordance with one or more embodiments of the disclosure.

At block 602 of method 600, the second end 308 (i.e., the distal tip) of the delivery tube 300 may be positioned adjacent to the one or more neural circuits. Upon positioning the distal tip of the delivery tube 300 adjacent to the one or more neural circuits at block 602, a first drug 122 may be administered to the one or more neural circuits by way of a first conduit 310 within the delivery tube 300 at block 604. That is, the first drug 122 may flow from the first reservoir 118, into the first chamber 136, down the first conduit 310, and be delivered to the targeted neural circuit by the second end 308 of the delivery tube 300 (i.e., the distal tip). At block 606 of method 600, a second drug 130 may be administered to the one or more neural circuits by way of a second conduit 312 within the delivery tube 300. That is, the second drug 130 may flow from the second reservoir 126, into the second chamber 138, down the second conduit 312, and be delivered to the targeted neural circuit by the second end 308 of the delivery tube 300 (i.e., the distal tip).

In certain embodiments, electrical stimulation is administered to the one or more neural circuits by way of an electrode 320 positioned within a third conduit 314 of the delivery tube 300. In this manner, the injectrode 500 can be used to administer precise, variable doses of chemical and electrical therapy to anatomically specific regions of the brain or elsewhere. The first drug 122, the second drug 130, and/or the electrical stimulation may be administered to the targeted neural circuit separately or simultaneously. In certain embodiments, the electrode 320 may be used to record local neural activity to provide feedback to optimize drug delivery parameters based on neural circuit behavior.

The steps described in blocks 604-608 of method 600 may be performed in any order. Moreover, certain steps may be omitted, while other steps may be added. For example, additional drugs may be administered to the one or more neural circuits and/or additional electrical stimulation may be applied to the one or more neural circuits.

The present disclosure is further illustrated by the following non-limiting examples.

Example 1

Injectrode Infusion Study

Preliminary studies using an injectrode as illustrated in FIG. 5 have yielded delivered volumes with moderate accuracy and reproducibility within about 5% of the desired volumes (Table 1). The data in Table 1 is from a single device. Each infusion volume was repeated in triplicate. The measured infusion volumes for each dye are consistent and include standard deviations of approximately about 5%. The micro syringe pumps used to control the infusion have quoted accuracies of about 3-5% of infusion volume. The injectrode therefore did not introduce a large degree of variability. The measured volumes for blue dye are consistently low due to dilution of the blue dye during loading.

TABLE 1

| Infusion results from the first two lumen device. | | | | | | | |
|---|---|---|---|---|---|---|---|
| Blue | | | | Red | | | |
| Target Volume (nl) | Average Measured Volume n = 3 (nl) | Standard Deviation (nl) | Standard Deviation as % | Target Volume (nl) | Average Measured Volume n = 3 (nl) | Standard Deviation (nl) | Standard Deviation as % |
| 300 | 262 | 11.6 | 4.43 | 300 | 305.6 | 20.2 | 6.6 |
| 200 | 183 | 4.64 | 2.53 | 200 | 212.5 | 6.1 | 2.9 |
| 100 | 89.1 | 4.66 | 5.23 | 100 | 102.5 | 3.0 | 2.9 |
| 50 | 47.9 | 1.4 | 2.96 | 50 | 59.1 | 3.0 | 5.1 |

Preliminary in vivo infusions in animal models have demonstrated that the injectrode is capable of safely infusing drug solutions to targeted neural circuits within the brain.

Example 2

In Vitro Brain Phantom Infusion

Figure 7:
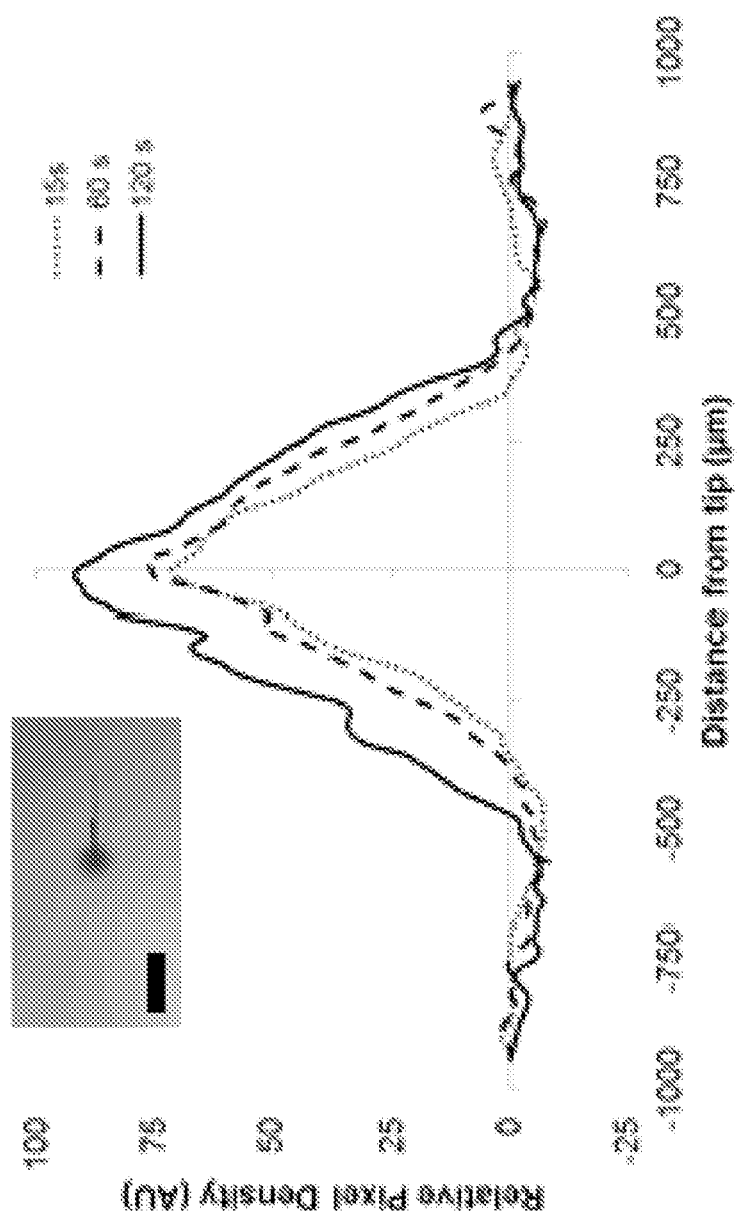
FIG. 7 depicts dye infusion in agarose phantom. Dye was infused into 0.6% agarose (400 nl total at 200 nl/min) Digital images were recorded and densitometry used to characterize radial concentration profiles. The peak width with these parameters is 1 mm. The inset in FIG. 7 is a representative image of dye plume after infusion. The injectrode catheter is seen coming from the left side of the image. (scale: 2 mm).

Tissue phantom infusion experiments were conducted to demonstrate device function in a medium that resembles brain tissue. Devices were inserted into an agarose gel in a way that represents how they will be implanted in vivo. Solutions of dye were infused, under the same parameters that may be used to target neural circuits in vivo (400 nL, 100 nL/min) The trajectory of dye was imaged using an optical microscope at multiple time points. Computer aided image analysis was used to characterize the spatial distribution of dye over time. FIG. 7 depicts the distribution of dye as a function of distance from the infusion site at multiple times over the infusion. The dye was observed to become infused to a radius of 0.5 mm from the injectrode center. This is similar to the dimensions of neural circuit foci. This experiment demonstrated that the injectrode is capable of releasing drug in the presence of a tissue phantom without clogging, and that the volume of tissue exposed to the drug can be effectively controlled by both the time infused or total infused volume.

Example 3

Acute and Chronic Device Function in Rodent Brain

Figure 8:
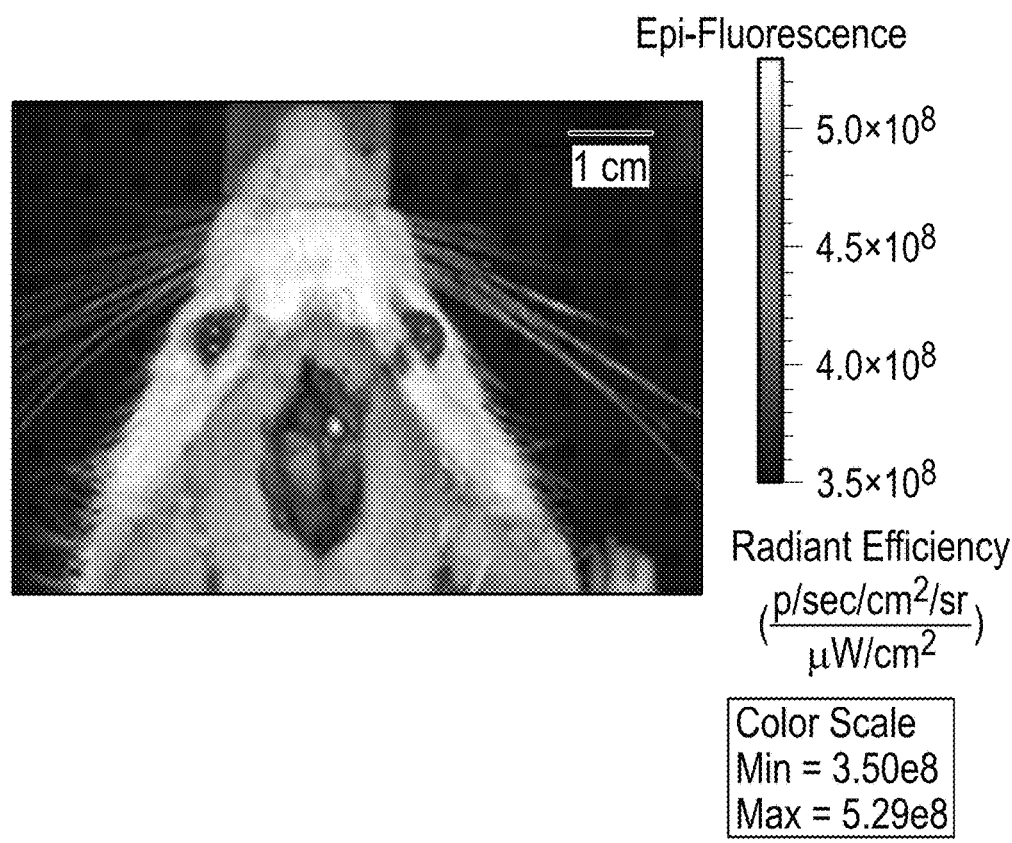
FIG. 8 depicts acute in vivo infusion, with an epifluorescent image (left) and a 3D reconstruction of transillumination images (right). Following craniotomy surgery, 1 µl of 0.5 mg/ml ICG was infused into the rodent striatum. The diameter of the fluorescent source as determined by 3D reconstruction was 2.1 mm and the center of the source was estimated to be 2.4 mm below the surface of the skull.
Figure 8:
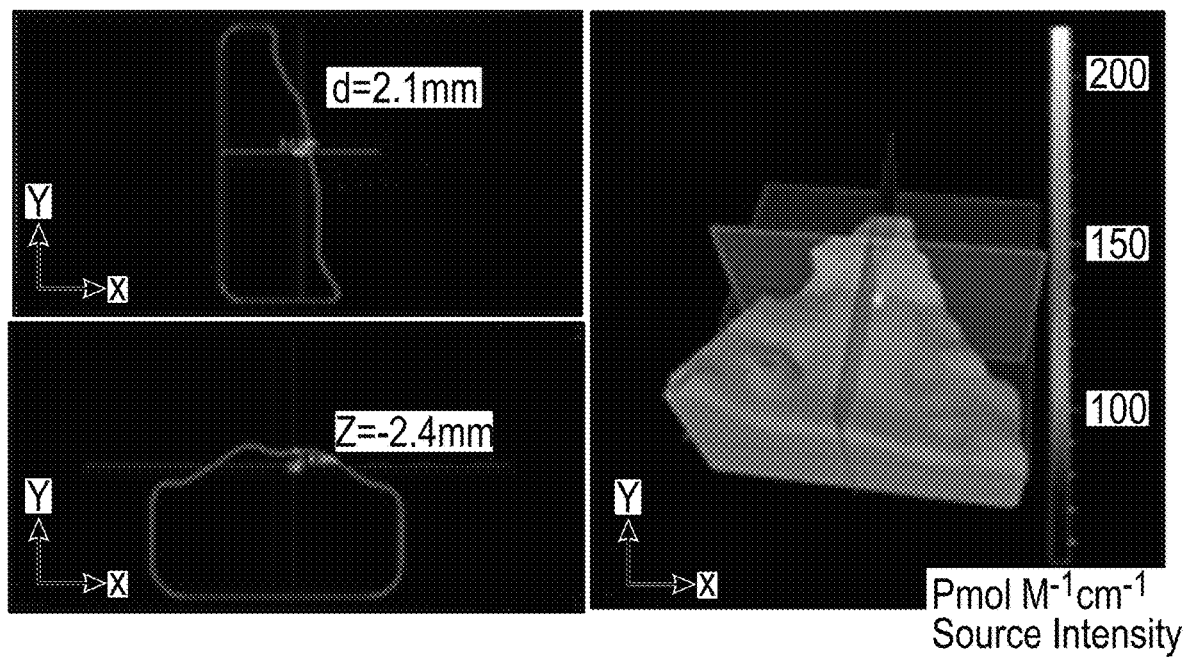

Preliminary acute infusions were conducted in which the injectrode device function was demonstrated in rodents. The objective of these experiments was to show that the device is capable of safely and reliably infusing a drug solution into the brain to modulate neural circuit activity. A solution containing a near IR dye was infused as a proxy for a drug solution. Adult rats were anesthetized and placed in a stereotactic frame. Following a craniotomy, the device was lowered into the striatum (2 mm below brain surface). 1 µl of the dye was infused at a flow rate of 100 nL/min, which were parameters expected to be suitable for targeting neural circuit structures. The anesthetized animal was transferred to the IVIS spectrum imaging system following infusion. Epifluorescent and transillumination fluorescent images were obtained. The transillumination images were used to produce a 3D reconstruction of the fluorescent source with Living Image analysis software. The obtained images are shown in FIG. 8. Measurements of the 3D reconstruction estimated the diameter of the fluorescent source to be 2.1 mm. This value agreed well with the expected value of 2.2 mm. The center of the fluorescent source was found to be 2.4 mm below the surface of the skull. This agrees with the stereotactic coordinates used in the infusion (2 mm below the surface of the brain+≈0.5 mm thick skull). These results demonstrate that the device is capable of safely infusing a solution to target a specific neural structure in the brain.

Figure 9:
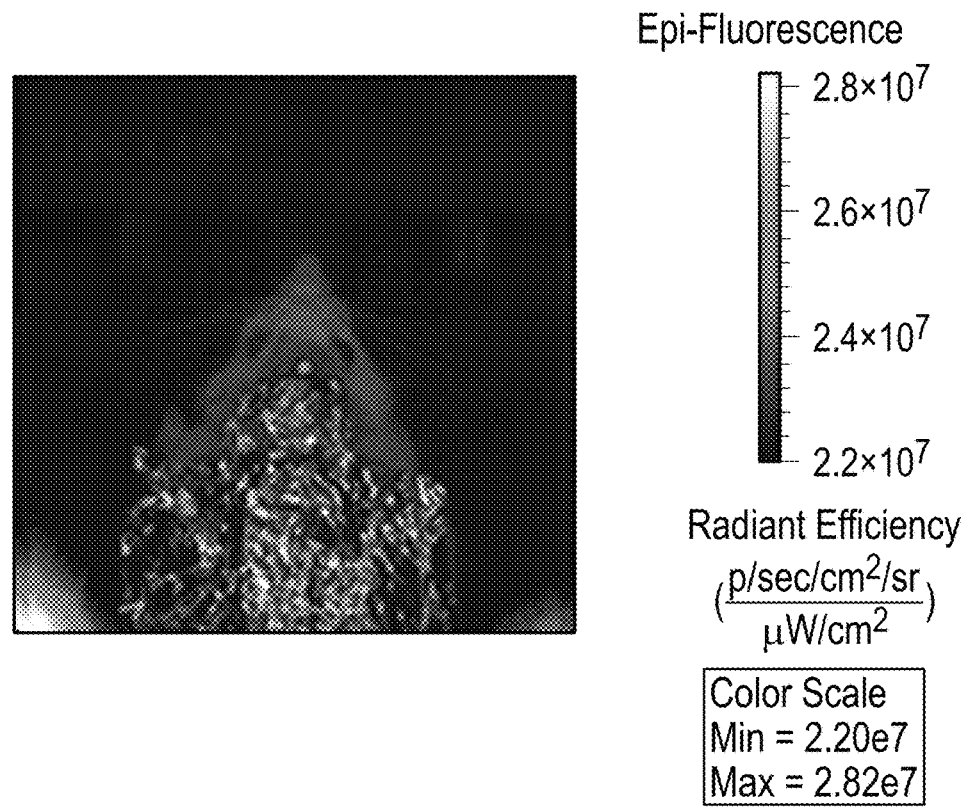
FIG. 9 depicts epifluorescent images (top-left, side view—right) of a near IR dye infusion following chronic injectrode implantation.
Figure 9:
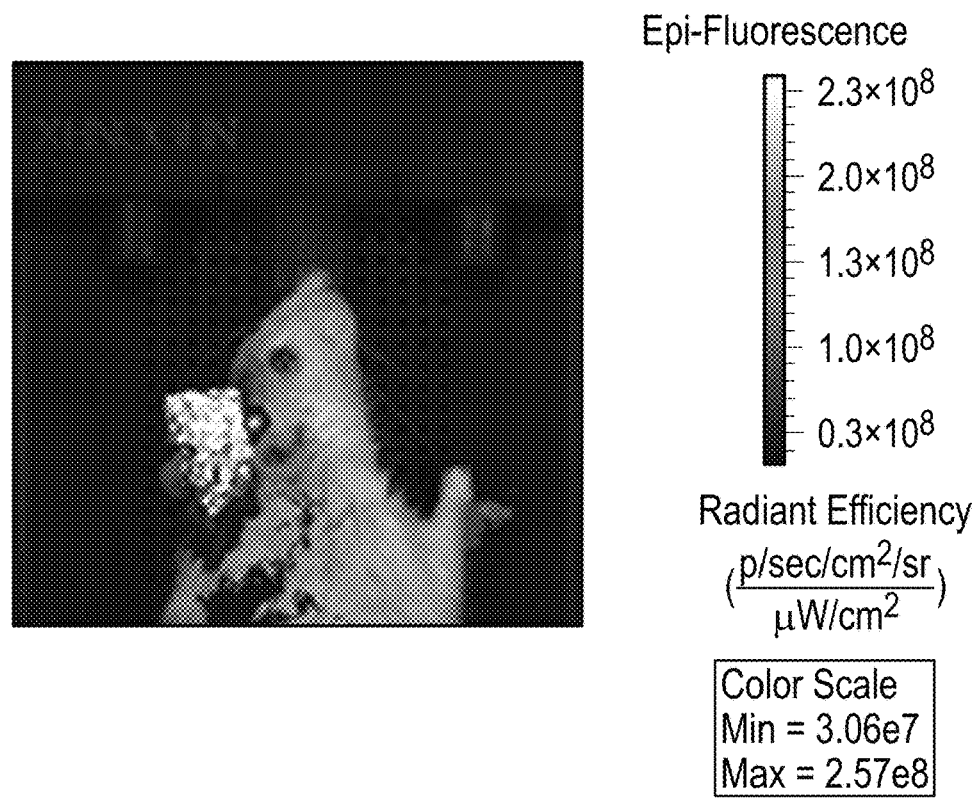

Protocols were developed to chronically implant the device into the rodent brain. The purpose of this experiment was to demonstrate the ability of the distal end of the injectrode to target various neural circuit components in the brain following chronic implantation. Adult male rats were anesthetized and placed in a stereotactic frame. Following a craniotomy, the device was lowered into the striatum and secured in place using a dental cement/gentamicin mixture. To confirm device function following implantation, 1 µl of a near infrared fluorescent dye was infused at a flow rate of 100 nL/min, which were parameters anticipated to be suitable for targeting specific structures of the brain implicated with neuropsychiatric disorders. Epifluorescent fluorescent images were obtained using the IVIS spectrum imaging system, as depicted in FIG. 9. These results demonstrate that the device is capable of safely infusing a solution following implantation. The device remained implanted for 8 weeks without any significant changes in animal behavior.

Example 4

Acute and Chronic Device Function in Rodent Brain

Figure 10:
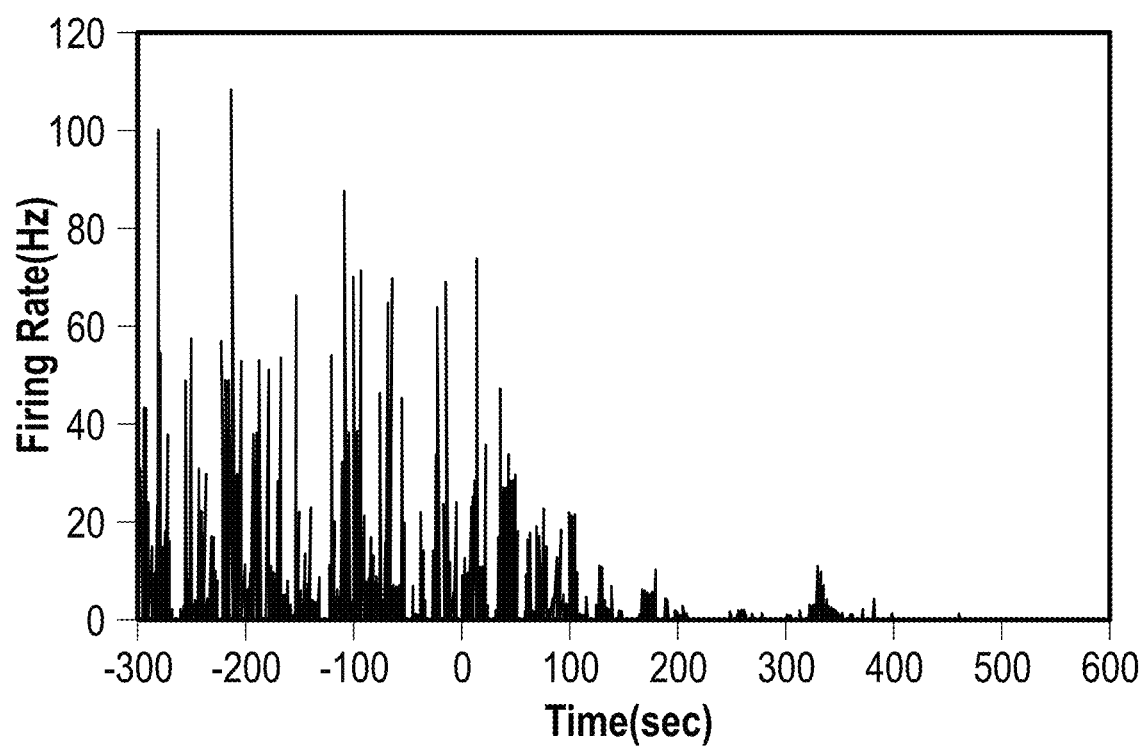
FIG. 10 depicts an example of neuronal silencing of monkey striatal medium spiny neurons in response to drug infusion. 200 nanoliters of drug was infused at time 0 over 2 minutes.

Infusion trials were also performed in a non-human primate. A version of the injectrode with a recording microelectrode in the third lumen and single lumen for drug delivery was acutely implanted on the animal's skull. 200 nanoliters of muscimol was infused into the striatum, a subcortical structure several centimeters deep into the brain. Muscimol is a GABA agonist which reduces the activity of the local neural tissue. The electrical activity of the local neurons was significantly reduced following drug infusion, as depicted in FIG. 10. This experiment establishes that the current design is safe for use in a much larger primate brain and is capable of modulating neural circuit activity.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments.

We claim:

1. An injectrode, comprising:
a manifold comprising a plurality of chambers therein, each of said chambers being isolated from one another; and
a delivery tube which extends partially into the manifold, the delivery tube comprising:
a plurality of fluid conduits, each of the plurality of fluid conduits being in fluid communication with a separate and single chamber of the plurality of chambers,
an electrode, and
at least one electrode conduit configured to house the electrode therein; and
a biocompatible metal guide tube positioned about the delivery tube,
wherein a distal tip of the delivery tube is configured to be positioned adjacent to one or more neural circuits for providing chemical stimulation, electrical stimulation, sensing of neural activity, or a combination thereof,
wherein each of the plurality of fluid conduits has a length of at least 5 cm and a volume μl hold up of less than 10 μL, and
wherein the plurality of chambers within the manifold are isolated from one another by at least one septum through which the delivery tube extends.

2. The injectrode of claim 1, wherein each fluid conduit of the plurality of fluid conduits comprises an access port through a side wall of the delivery tube configured to be positioned within the single chamber of the plurality of chambers with which said fluid conduit is in fluid communication.

3. The injectrode of claim 1, wherein the guide tube comprises stainless steel.

4. The injectrode of claim 1, wherein the guide tube is from about 180 μm to about 220 μm in diameter.

5. The injectrode of claim 1, wherein each of two of the plurality of chambers respectively is in further fluid communication with one of two separate fluid reservoirs.

6. The injectrode of claim 1, wherein each of the plurality of conduits has an outlet at the distal tip end of the delivery tube and wherein the outlet has a diameter from 10 μm to 100 μm.

7. The injectrode of claim 1, wherein the delivery tube is formed of borosilicate glass.

8. The injectrode of claim 1, wherein the plurality of chambers comprises a first chamber and a second chamber.

9. The injectrode of claim 8, wherein a first conduit of the plurality of conduits is in fluid communication with the first chamber but not with the second chamber, and wherein a second conduit of the plurality of conduits is in fluid communication with the second chamber but not with the first chamber.

10. The injectrode of claim 8, further comprising a third chamber positioned between the first chamber and second chamber, wherein the third chamber is configured to separate the first chamber from the second chamber.

11. The injectrode of claim 10, wherein the first chamber, the second chamber, and the third chamber are separated by one or more silicone septum partitions.

12. The injectrode of claim 9, wherein the first conduit comprises a first access port configured to be positioned within the first chamber, and wherein the second conduit comprises a second access port configured to be positioned within the second chamber.

13. The injectrode of claim 1, wherein the delivery tube has:
(a) a length from about 8 cm to about 16 cm,
(b) a diameter from about 100 μm to about 200 μm, or
(c) a length from about 8 cm to about 16 cm and a diameter from about 100 μm to about 200 μm.

14. The injectrode of claim 1, wherein the at least one electrode conduit is from about 80 μm to about 100 μm in diameter.

15. The injectrode of claim 1, wherein the electrode comprises a tungsten electrode or carbon fiber.

16. The injectrode of claim 1, wherein the electrode is about 75 micrometers in diameter.

17. The injectrode of claim 1, wherein each of the plurality of fluid conduits is from about 20 μm to about 50 μm in diameter.

18. The injectrode of claim 1, wherein each of the plurality of fluid conduits has a length of at least 10 cm.

19. The injectrode of claim 1, wherein each of the plurality of fluid conduits has a volume hold up between about 1 μL to and about 5 μL.

20. The injectrode of claim 19, wherein each of the plurality of fluid conduits has a volume hold up of about 1 μL.

21. An injectrode, comprising:
a manifold which comprises a plurality of chambers therein, each of said chambers being isolated from one another by at least one silicone septum; and
a borosilicate delivery tube, which extends into the manifold and through the at least one silicone septum, the delivery tube comprising:
a plurality of conduits extending axially through the delivery tube, each of said conduits being in fluid communication with a separate and single chamber of the plurality of chambers of the manifold, and
at least one electrode conduit housing an electrode therein,
wherein the delivery tube has a length of at least 10 cm and a diameter between about 120 μm and about 180 μm, and
wherein a distal tip of the delivery tube is configured to be positioned adjacent to one or more neural circuits for providing chemical stimulation, electrical stimulation, sensing of neural activity, or a combination thereof.

22. The injectrode of claim 21, further comprising a metal guide tube positioned about the delivery tube.

23. A method for delivering chemical and electrical stimulation across one or more neural circuits, the method comprising:
positioning the distal tip of the delivery tube of the injectrode of claim 21 adjacent to the one or more neural circuits;
providing a first drug to the one or more neural circuits by way of a first conduit within the delivery tube;
providing a second drug to the one or more neural circuits by way of a second conduit within the delivery tube; and
providing electrical stimulation to the one or more neural circuits by way of an electrode positioned within a third conduit within the delivery tube.

24. A method for delivering chemical stimulation across and electrical contact with one or more neural circuits, the method comprising:
- positioning the distal tip of the delivery tube of the injectrode of claim 21 adjacent to the one or more neural circuits within a patient;
- delivering a first drug through a first conduit within the delivery tube selectively to the one or more neural circuits; and
- placing into electrical engagement with the one or more neural circuits an electrode which extends through a second conduit within the delivery tube.

25. The method of claim 24, further comprising delivering a second drug through a third conduit within the delivery tube selectively to the one or more neural circuits.

26. The method of claim 24, further comprising using the electrode to sense and record neural activity of the one or more neural circuits.

27. The method of claim 24, further comprising using the electrode to selectively deliver electrical stimulation to the one or more neural circuits.

\* \* \* \* \*